(12) United States Patent  (10) Patent No.: US 8,008,019 B2
Merante et al.  (45) Date of Patent: Aug. 30, 2011

(54) USE OF DUAL-TAGS FOR THE EVALUATION OF GENOMIC VARIABLE REPEAT REGIONS

(75) Inventors: Frank Merante, Etobicoke (CA); Susan Bortolin, Oakville (CA); Barbara Galvan-Goldman, Etobicoke (CA)

(73) Assignee: Luminex Molecular Diagnostics, Toronto (CA)

( * ) Notice: Subject to any disclaimer, the term of this patent is extended or adjusted under 35 U.S.C. 154(b) by 300 days.

(21) Appl. No.: 12/277,768

(22) Filed: Nov. 25, 2008

(65) Prior Publication Data

US 2009/0136956 A1  May 28, 2009

Related U.S. Application Data

(60) Provisional application No. 60/990,836, filed on Nov. 28, 2007.

(51) Int. Cl.
 *C12Q 1/68* (2006.01)
 *C12P 19/34* (2006.01)
(52) U.S. Cl. ...................................... 435/6.12; 435/91.2
(58) Field of Classification Search .............. 435/6, 91.2
 See application file for complete search history.

(56) References Cited

U.S. PATENT DOCUMENTS

| | | | |
|---|---|---|---|
| 5,525,494 A | 6/1996 | Newton | 435/91.2 |
| 5,736,330 A | 4/1998 | Fulton | 435/6 |
| 5,981,180 A | 11/1999 | Chandler et al. | 435/6 |
| 6,057,107 A | 5/2000 | Fulton | 435/6 |
| 7,226,737 B2 | 6/2007 | Pancoska et al. | 435/6 |
| 2005/0191625 A1 | 9/2005 | Kobler et al. | 435/6 |
| 2005/0191636 A1* | 9/2005 | Hahn | 435/6 |

* cited by examiner

*Primary Examiner* — Kenneth R. Horlick
(74) *Attorney, Agent, or Firm* — Fulbright & Jaworski LLP

(57) ABSTRACT

The methods and compositions of the present invention allow for the evaluation of a nucleotide expansion, contraction or deletion. In one embodiment, the present invention provides a method for detecting a nucleotide expansion, contraction or deletion comprising amplifying a target nucleic acid sequence with a primer pair, each primer comprising a target specific sequence and a differentiating tag sequence, labeling the target nucleic acid sequence to produce a dual-tagged amplification product; digesting the dual-tagged amplification product to produce an expansion region fragment and an internal control fragment; hybridizing the fragments to separate capture complexes; detecting the signals produced by the labels on the immobilized fragments and comparing the intensity of the signals to detect the nucleotide expansion, contraction or deletion region.

24 Claims, 2 Drawing Sheets ctccgtttcggtttcacttccggtggagggccgcctctgagcgggcggcgggccgacggcgagcgcgggcggcggcggtgacggag
gcgccgctgccagggggcgtgcggcagcgcggcggcggcggcggcggcggcggcggcggaggcggcggcggcggcggcggc
ggcgg(cgg)ₙctgggccfcgagcgcccgcagcccacctctcggggcgggctcccggcgctagcagggctgaagagaagat

FIG. 1

FMR1-expand-Tag-PCR-Forw (RVM-9)
 AACTTTCTCTCTATTCTTATTT/iSp18/CTCCGTTTCGGTTTCACTTC
  [Tag on Forward Primer]   [Blocker]   [Gene-Specific Primer]

FMR1-expand-Tag-PCR-Rev (RVM-7)
 AATTTCTTCTTTCTTTCACAAT/iSp18/ATCTTCTCTTCAGCCCTGCT
  [Tag on Reverse Primer]   [Blocker]   [Gene-Specific Primer]

FIG. 2

SEQUENCE LISTING

```
<160> NUMBER OF SEQ ID NOS: 5

<210> SEQ ID NO 1
<211> LENGTH: 44
<212> TYPE: DNA
<213> ORGANISM: Artificial
<220> FEATURE:
<223> OTHER INFORMATION: Synthetic primer

<400> SEQUENCE: 1
aactttctct ctctattctt atttctccgt ttcggtttca cttc            44

<210> SEQ ID NO 2
<211> LENGTH: 44
<212> TYPE: DNA
<213> ORGANISM: Artificial
<220> FEATURE:
<223> OTHER INFORMATION: Synthetic primer

<400> SEQUENCE: 2
aatttcttct ctttctttca caatatcttc tcttcagccc tgct            44

<210> SEQ ID NO 3
<211> LENGTH: 247
<212> TYPE: DNA
<213> ORGANISM: Artificial
<220> FEATURE:
<223> OTHER INFORMATION: Synthetic primer
<220> FEATURE:
<221> NAME/KEY: misc_feature
<222> LOCATION: (176)..(176)
<223> OTHER INFORMATION: n is a, c, g, or t

<400> SEQUENCE: 3
ctccgtttcg gtttcacttc cggtggaggg ccgcctctga gcgggcggcg ggccgacggc    60
```

```
gagcgcgggc ggcggcggtg acggaggcgc cgctgccagg gggcgtgcgg cagcgcggcg      120
gcggcggcgg cggcggcggc ggcggaggcg gcggcggcgg cggcggcggc ggcggnctgg      180
gcctcgagcg cccgcagccc acctctcggg ggcgggctcc cggcgctagc agggctgaag      240
agaagat                                                                247

<210> SEQ ID NO 4
<211> LENGTH: 60
<212> TYPE: DNA
<213> ORGANISM: Artificial
<220> FEATURE:
<223> OTHER INFORMATION: Synthetic primer

<400> SEQUENCE: 4
cccccgcacg ccgtcgcgcc gccgccgccg ccgccgctgc cgccgccgcc gctgccgccg       60

<210> SEQ ID NO 5
<211> LENGTH: 103
<212> TYPE: DNA
<213> ORGANISM: Artificial
<220> FEATURE:
<223> OTHER INFORMATION: Synthetic primer
<220> FEATURE:
<221> NAME/KEY: misc_feature
<222> LOCATION: (90)..(90)
<223> OTHER INFORMATION: n is a, c, g, or t

<400> SEQUENCE: 5
gcgccgctgc caggggggcgt gcggcagcgc ggcggcggcg gcggcggcgg cggcggcgga       60
ggcggcggcg gcggcggcgg cggcggcggn ctgggcctcg agc                         103
```

USE OF DUAL-TAGS FOR THE EVALUATION OF GENOMIC VARIABLE REPEAT REGIONS

This application claims priority to U.S. Application No. 60/990,836, filed on Nov. 28, 2007, the entire disclosure of which is incorporated by reference.

BACKGROUND OF THE INVENTION

A. Field of the Invention

The present invention relates generally to the fields of genetics and molecular biology. More particularly, it concerns genetic screening. In specific embodiments, the invention concerns methods for evaluating a nucleotide expansion, contraction or deletion within a target nucleic acid sequence.

B. Description of Related Art

It has been established that the human genome is not a static entity. Repeating units of about 1 to 4 base pairs in length are particularly prone to instability, which leads to greater variability in the genome. This variability can produce polymorphic loci (e.g., microsatellites, short tandem repeats) that are useful as molecular markers in genetic studies. Additionally, particular diseases arise due to genome instability manifested as nucleotide expansions, contractions or deletions. An example of such a disease is the Fragile-X syndrome. In this case, expansion of a repeating motif $(CGG)_n$ in the FMR1 gene, residing on the X-chromosome, can give rise to a pleotrophic phenotype resulting in mild to severe mental retardation. Nucleotide expansions also have been associated with Huntington's Disease (HD) and SBMA (Spinobulbar Muscular Atrophies; SCA1 to SCA8). Additional non-limiting examples of diseases associated with repeat expansions are Dentatrubrual-Pallidoluysian Atrophy, Myotonic Dystrophy, Ataxia syndromes (i.e., Friedrich's syndrome) and Androgen Receptor Disfunction. Telomeric repeat lengths may be correlated to senescence (or the lack thereof).

Generally, high resolution electrophoretic methods, including sequencing, are used to quantify the number of repeats present in an expansion region of a gene. Although very accurate, these methods are slow, expensive and cumbersome for general screening. A method suitable for mass screening and preliminary segregation of samples is therefore needed.

SUMMARY OF THE INVENTION

The methods and compositions of the present invention allow the evaluation of an expansion, contraction or deletion region in a nucleic acid sequence. In one embodiment, the present invention provides a method for determining the presence and size of a nucleotide expansion, contraction or deletion region within a target nucleic acid sequence comprising amplifying a target nucleic acid sequence with a primer pair, each primer of the primer pair comprising a target specific sequence, a differentiating tag sequence 5' of the target specific sequence and a blocker between the target specific sequence and the differentiating tag sequence to produce a dual-tagged amplification product; labeling the dual-tagged amplification product; digesting the dual-tagged amplification product with a restriction enzyme to produce a variation region fragment and an internal control fragment; hybridizing the variation region fragment to a first capture complex comprising an anti-tag sequence and a solid support, and hybridizing the internal control fragment to a second capture complex comprising an anti-tag sequence and a solid support; detecting a signal produced by the label or labels on the immobilized variation region fragment and the internal control fragment; and comparing the intensity of the signal of the variation region fragment and the internal control fragment to determine the size of the nucleotide expansion, contraction or deletion region.

The expansion or contraction may be in a repetitive nucleic acid sequence. The repetitive sequence may comprise, for example, repeating units of 1, 2, 3, 4, 5, or 6 nucleotides. In certain aspects, the expansion may be a trinucleotide expansion or a dinucleotide expansion. For example, the expansion may be the CGG trinucleotide repeat region of the FMR1 gene. Other non-limiting examples of tri-nucleotide expansion diseases that may be screened for by the current invention include Dentatorubropallidoluysian atrophy (CAG trinucleotide repeat in DRPLA gene), Huntington's disease (CAG trinucleotide repeat in the huntington gene), Spinobulbar muscular atrophy (CAG trinucleotide repeat in Androgen receptor gene on the X chromosome), SCA1 (Spinocerebellar ataxia Type 1) (CAG trinucleotide repeat), SCA2 (Spinocerebellar ataxia Type 2) (CAG trinucleotide repeat), SCA3 (Spinocerebellar ataxia Type 3 or Machado-Joseph Disease) (CAG trinucleotide repeat), SCA6 (Spinocerebellar ataxia Type 6) (CAG trinucleotide repeat), SCA7 (Spinocerebellar ataxia Type 7) (CAG trinucleotide repeat), SCA17 (Spinocerebellar ataxia Type 17) (CAG trinucleotide repeat), FRAXE (Fragile XE mental retardation) (GCC trinucleotide repeat in FMR2 on the X chromosome), Friedreich's ataxia (GAA trinucleotide repeat in X25 (frataxin) gene), Myotonic dystrophy (CTG trinucleotide repeat in DMPK gene), SCA8 (Spinocerebellar ataxia Type 8) (CTG trinucleotide repeat), SCA12 (Spinocerebellar ataxia Type 12) (CAG trinucleotide repeat). Additional non-limiting examples of diseases associated with repeat expansions are Dentatrubrual-Pallidoluysian Atrophy, and Androgen Receptor Disfunction. Telomeric repeat lengths may be correlated to senescence (or the lack thereof). The contraction may be, for example, SCA8 CTG repeats (Moseley et al., 2000). The deletion may be, for example, Duchenne muscular dystrophy (Gatta et al., 2005)

In one embodiment, the invention provides a method for evaluating the length of a trinucleotide repeat region on an X chromosome comprising amplifying a trinucleotide repeat region on the X chromosome with a primer pair, each primer of the primer pair comprising a target specific sequence, a differentiating tag sequence 5' of the target specific sequence and a blocker between the target specific sequence and the differentiating tag sequence to produce a dual-tagged amplification product; labeling the dual-tagged amplification product; digesting the dual-tagged amplification product with a restriction enzyme to produce a trinucleotide repeat region fragment and an internal control fragment; hybridizing the trinucleotide repeat region fragment to a first capture complex comprising an anti-tag sequence and a solid support, and hybridizing the internal control fragment to a second capture complex comprising an anti-tag sequence and a solid support; detecting a signal produced by the labels on the immobilized trinucleotide repeat region fragment and the internal control fragment; and comparing the intensity of the signal of the trinucleotide repeat region fragment and the internal control fragment to evaluate the length of the trinucleotide repeat region on the X chromosome. In certain aspects, the trinucleotide repeat region on the X chromosome is a trinucleotide repeat region of an FMR1 gene, an FMR2 gene or an Androgen Receptor gene. In some aspects, the length of the trinucleotide repeat region is evaluated semi-quantitatively as being normal, pre-expansion, or expanded.

In another embodiment, the invention provides a method for diagnosing a trinucleotide expansion disease on the X chromosome comprising obtaining a sample from a subject to be tested; amplifying a target nucleic acid sequence with a primer pair, each primer of the primer pair comprising a target specific sequence, a differentiating tag sequence 5' of the target specific sequence and a blocker between the target specific sequence and the differentiating tag sequence to produce a dual-tagged amplification product; labeling the dual-tagged amplification product; digesting the dual-tagged amplification product with a restriction enzyme to produce an expansion region fragment and an internal control fragment; hybridizing the expansion region fragment to a first capture complex comprising an anti-tag sequence and a solid support, and hybridizing the internal control fragment to a second capture complex comprising an anti-tag sequence and a solid support; detecting a signal produced by the labels on the immobilized expansion region fragment and the internal control fragment; and comparing the intensity of the signal of the expansion region fragment and the internal control fragment to diagnose a trinucleotide expansion disease if the intensity of the signal of the expansion region fragment is above a pre-determined threshold value. The disease may be, for example, Fragile-X syndrome, Fragile XE mental retardation, or spinobulbar muscular atrophy.

The target nucleic acid sequence may be any sequence of interest that contains or is suspected of containing an expansion, contraction or deletion. For example, the methods of the present invention may be used in genetic screening for trinucleotide or dinucleotide expansion diseases. In certain aspects of the invention, the sample is a sample being screened for the presence or absence of an expanded trinucleotide repeat region of the FRM1 gene. In further aspects of the invention, the target sequence is on the X chromosome. For example, a target sequence on the X chromosome may include all or part of a FMR1, FMR2, and/or androgen receptor gene. Additional, potential targets are the genes associated with Huntington's Disease (HD), SBMA (Spinobulbar Muscular Atrophies; SCA1 to SCA8), Dentatrubrual-Pallidoluysian Atrophy, Myotonic Dystrophy, and Ataxia syndromes (i.e., Friedrich's syndrome).

The sample containing the target nucleic acid sequence may be any sample that contains nucleic acids. In certain aspects of the invention, the sample is a sample being evaluated for a nucleotide expansion, contraction or deletion. The sample may be from any mammalian creature. In a one embodiment, the sample is from a human. In a further embodiment, the sample is from a male. Where the sample is obtained from a subject, it may be obtained by methods known to those in the art such as swabbing or venipuncture.

In one embodiment, the present invention provides a method for evaluating a $(CGG)_n$ expansion region within an FMR1 gene comprising amplifying a $(CGG)_n$ expansion region within an FMR1 gene with a primer pair, each primer of the primer pair comprising a target specific sequence, a differentiating tag sequence 5' of the target specific sequence and a blocker between the target specific sequence and the differentiating tag sequence to produce a dual-tagged amplification product; labeling the dual-tagged amplification product; digesting the dual-tagged amplification product with a restriction enzyme to produce an expansion region fragment and an internal control fragment; hybridizing the expansion region fragment to a first capture complex comprising an anti-tag sequence and a solid support, and hybridizing the internal control fragment to a second capture complex comprising an anti-tag sequence and a solid support; detecting a signal produced by the labels on the immobilized expansion region fragment and the internal control fragment; and comparing the intensity of the signal of the expansion region fragment and the internal control fragment to evaluate the $(CGG)_n$ expansion region within the FMR1 gene.

In another embodiment, the invention provides a method for diagnosing Fragile-X syndrome comprising obtaining a nucleic acid sample from a subject to be tested; amplifying a $(CGG)_n$ expansion region within an FMR1 gene with a primer pair, each primer of the primer pair comprising a target specific sequence, a differentiating tag sequence 5' of the target specific sequence and a blocker between the target specific sequence and the differentiating tag sequence to produce a dual-tagged amplification product; labeling the dual-tagged amplification product; digesting the dual-tagged amplification product with a restriction enzyme to produce an expansion region fragment and an internal control fragment; hybridizing the expansion region fragment to a first capture complex comprising an anti-tag sequence and a solid support, and hybridizing the internal control fragment to a second capture complex comprising an anti-tag sequence and a solid support; detecting a signal produced by the labels on the immobilized expansion region fragment and the internal control fragment; and comparing the intensity of the signal of the expansion region fragment and the internal control fragment to diagnose Fragile-X syndrome if the intensity of the signal of the expansion region fragment is above a pre-determined threshold value. The above method may also be employed to detect pre-expansion of the trinucleotide repeat region of FMR1.

The primer pairs are designed to amplify the target nucleic acid sequence. Accordingly, each of the primers contains a target specific sequence, which selectively hybridizes to a sequence on the target. The pair of primers are designed such that together they flank the expansion, contraction or deletion region of the target nucleic acid sequence that is to be studied. Further, the primers should amplify a sequence that includes a restriction site suitable for creating a variation region fragment and an internal control region fragment when cleaved. Accordingly, this restriction site should only occur outside of the variation region, such that upon cleaving the amplification product there is a fragment comprising the variation region and a fragment comprising an internal control region. In one embodiment, the primer pair comprise SEQ ID NO: 1 and SEQ ID NO:2.

A differentiating tag sequence is located 5' of the target specific sequence on each primer in the primer pair. Amplification of the target nucleic acid sequence with the primer pair will, therefore, result in an amplification product with two different tag sequences. Each differentiating tag sequence is the complement of an anti-tag sequence of the capture complex. Specific hybridization between each tag sequence and the anti-tag sequence allows for the capture of the amplified target nucleic acid sequence by the capture complex. A number of tag and tag complement (anti-tag) sequences are known in the art and may be used in the present invention. For example, U.S. Pat. No. 7,226,737, incorporated herein by reference, describes a set of 210 non-cross hybridizing tags and anti-tags. In addition, U.S. Published Application No. 2005/0191625, incorporated herein by reference, discloses a family of 1168 tag sequences with a demonstrated ability to correctly hybridize to their complementary sequences with minimal cross hybridization.

Following the initial extension of the primer comprising the tag sequence, the tagged extension product may serve as a template for the other primer of the primer pair. It may be undesirable, however, for the extension from such a template to proceed through the tag region as this can interfere with the hybridization of the tag sequence with the anti-tag sequence of the capture complex. Accordingly, a blocker can be positioned between the target specific sequence and the tag sequence of the primer. The blocker moiety inhibits extension through the tag sequence during second strand synthesis. Non-limiting examples of blocker moieties include C6-20 straight chain alkylenes, iSp18 (which is an 18-atom hexaethyleneglycol), and an oligonucleotide sequence in the reverse orientation as compared to the target specific sequence. Where the blocker moiety is an oligonucleotide sequence in the reverse orientation as compared to the target specific sequence, the blocker moiety and the tag sequence may be the same—in other words, the tag sequence is placed in the opposite orientation to the target specific sequence, which inhibits polymerase extension into the tag sequence. It is also possible to omit the blocker moiety from the primer. In this case, steps are taken to permit the hybridization of the tag sequence with the anti-tag sequence. The double-stranded amplification product, which contains an anti-tag/tag region at each end, may be denatured to render the DNA strands single stranded prior to hybridization to the appropriate anti-tag coupled to the solid substrate. As an alternative to denaturation, enzymatic treatment of the double-stranded amplification product may be used to eliminate the anti-tag containing strands.

In one embodiment, the labeling of the dual-tagged amplification product occurs during amplification. For example, amplification may occur in the presence of a reporter molecule which labels the dual-tagged amplification product. In a further embodiment, the labeling of the dual-tagged amplification product occurs after amplification. For instance, following amplification the dual-tagged amplification product may be denatured and a plurality of short fragments complementary to the expansion region of the target gene that are labeled with a reporter may be hybridized to the dual-tagged amplification product.

A reporter is a molecule that facilitates the detection of a molecule to which it is attached. Numerous reporter molecules that may be used to label nucleic acids are known. Direct reporter molecules include fluorophores, chromophores, and radiophores. Non-limiting examples of fluorophores include, a red fluorescent squarine dye such as 2,4-Bis[1,3,3-trimethyl-2-indolinylidenemethyl]cyclobutenediylium-1,3-dioxolate, an infrared dye such as 2,4 Bis[3,3-dimethyl-2-(1H-benz[e]indolinylidenemethyl)]cyclobutenediylium-1,3-dioxolate, or an orange fluorescent squarine dye such as 2,4-Bis[3,5-dimethyl-2-pyrrolyl]cyclobutenediylium-1,3-diololate. Additional non-limiting examples of fluorophores include quantum dots, Alexa Fluor® dyes, AMCA, BODIPY® 630/650, BODIPY® 650/665, BODIPY®-FL, BODIPY®-R6G, BODIPY®-TMR, BODIPY®-TRX, Cascade Blue®, CyDye™, including but not limited to Cy2™, Cy3™, and Cy5™, a DNA intercalating dye, 6-FAM™, Fluorescein, HEX™, 6-JOE, Oregon Green® 488, Oregon Green® 500, Oregon Green® 514, Pacific Blue™, REG, phycobilliproteins including, but not limited to, phycoerythrin and allophycocyanin, Rhodamine Green™, Rhodamine Red™, ROX™, TAMRA™, TET™, Tetramethylrhodamine, or Texas Red®. Indirect reporter molecules include biotin, which must be bound to another molecule such as streptavidin-phycoerythrin for detection.

The dual-tagged amplification product is digested with a restriction enzyme that recognizes a restriction site that will cleave the amplification product to produce a variation region fragment and an internal control fragment, each of which are differentially tagged. The length of the expansion, contraction or deletion is reflected in the variation region fragment while the length of the internal control fragment does not vary regardless of the size of the expansion, contraction or deletion.

As mentioned above, a differentiating tag sequence is located 5' of the target specific sequence on each primer in the primer pair. Each tag sequence is the complement of a separate anti-tag sequence, which is immobilized on a solid support. Specific hybridization between each tag sequence and its corresponding anti-tag sequence allows for the capture of the amplified target nucleic acid sequence by the capture complex. As mentioned above, a number of tag and tag complement sequences are known in the art and may be used in the present invention. For example, U.S. Pat. No. 7,226,737 describes a set of 210 non-cross hybridizing tags and anti-tags. In addition, U.S. Published Application No. 2005/0191625 discloses a family of 1168 tag sequences with a demonstrated ability to correctly hybridize to their complementary sequences with minimal cross hybridization. The capture complex comprises an anti-tag sequence and a solid support. Non-limiting examples of solid supports include: nitrocellulose, nylon membrane, glass, activated quartz, activated glass, polyvinylidene difluoride (PVDF) membrane, polystyrene substrates, polyacrylamide-based substrate, other polymers, copolymers, or crosslinked polymers such as poly(vinyl chloride), poly(methyl methacrylate), poly(dimethyl siloxane), photopolymers (which contain photoreactive species such as nitrenes, carbenes and ketyl radicals capable of forming covalent links with target molecules). A solid support may be in the form of a bead (microsphere), or a chip. Where the solid support is a bead, the anti-tag sequences on a given bead will typically be identical. Where the solid support is a chip, a plurality of different anti-tag sequences may be on the chip, but identical anti-tag sequences typically will be in spatially defined regions.

The beads of the capture complex may be encoded such that one subpopulation of beads can be distinguished from another subpopulation. Encoding may be by a variety of techniques. For example, the beads may be fluorescently labeled with fluorescent dyes having different emission spectra and/or different signal intensities. In certain embodiments, the beads are Luminex FlexMAP™ microspheres or Luminex xMAP® microspheres. The size of the beads in a subpopulation may also be used to distinguish one subpopulation from another. Another method of modifying a bead is to incorporate a magnetically responsive substance, such as $Fe_3O_4$, into the structure. Paramagnetic and superparamagnetic microspheres have negligible magnetism in the absence of a magnetic field, but application of a magnetic field induces alignment of the magnetic domains in the microspheres, resulting in attraction of the microspheres to the field source. Combining fluorescent dyes, bead size, and/or magnetically responsive substances into the beads can further increase the number of different subpopulations of beads that can be created.

Detection of the amplified target nucleic acid may be by a variety of techniques. In one aspect of the invention, the amplified target nucleic acids are detected using a flow cytometer. Flow cytometry is particularly well-suited where the solid support of the capture complex is a bead or other particle. In other aspects of the invention, detecting the amplified target nucleic acid comprises imaging the amplified target nucleic acid sequence bound to the capture complex. The imaging may be on, for example, a bead array platform or a chip array platform.

The intensities of the signals of the variation region fragment and the internal control fragment are compared to evaluate the nucleotide expansion, contraction or deletion region.

As mentioned above, following digestion the variation region fragment and the internal control fragment each remain labeled with the reporter molecule. The variation region fragment and the internal control fragment are hybridized to separate anti-tag sequences via their respective tag sequences. The anti-tag sequences are immobilized on a solid support. Where the solid support is a bead, the anti-tag sequences on a given bead will typically be identical. Where the solid support is a chip, a plurality of different anti-tag sequences may be on the chip, but they typically will be in spatially defined regions. The intensities of the signal of the variation region fragment and the internal control fragment will reflect the number of labeled residues found on each fragment. The variation region fragment will have an amount of reporter molecules that is related to the length of the expansion, contraction or deletion region, while the internal control fragment will have a constant number of labeled residues. The effect of the abundance of the amplification product on the signal intensity is adjusted for by the invariable length of the internal control fragment. Evaluation of the ratio of the median signal intensity between variation region fragment and the internal control fragment allow further evaluation of the region.

The evaluation may be quantitative or semi-quantitative. In many applications, a semi-quantitative evaluation is sufficient to identify which samples contain regions that contain an abnormal variation region. In a one embodiment, a semi-quantitative evaluation may be performed by direct comparison of the median fluorescence intensity (MFI) of the variation region fragment to the MFI of the internal control fragment. For example, a sample may be semi-quantitatively screened for an expanded trinucleotide repeat region of the FRM1 gene. A normal FMR1 gene typically contains between about 5 and 44 CGG repeats, whereas in people with Fragile X the FMR1 typically has over 200 CGG repeats. Thus, a threshold MFI ratio (expansion region/internal control) can be determined whereby if the MFI ratio is above this threshold it indicates an abnormal expansion and if it is below this level it indicates a normal repeat size. Certain expansion diseases also have what may be referred to as a "pre-expansion" size. For example, mothers of individuals affected by Fragile X syndrome have been found to have between about 60 and 200 CGG repeats. Thus, in certain embodiments, a threshold MFI ratio can be determined between a normal repeat size and a pre-expansion repeat size and/or between a pre-expansion repeat size and an abnormal expansion size. Accordingly, a semi-quantitative method may be used to classify a target nucleic acid sample as normal, pre-expansion, or abnormally expanded without needing to identify the precise number of repeats. Threshold MFI ratios may be determined by, for example, assaying target nucleic acids having expansion sizes of known lengths.

Alternatively, the method could provide a quantitative evaluation of the expansion, contraction or deletion in a nucleic acid sequence. In this instance, a series of standards comprising a collection of trinucleotide expansions can be run along side the query sample to quantitatively determine the repeat length of the unknown. The standards can be generated from synthetic material so that the necessary characteristics of the authentic trinucleotide repeat are maintained. Each periodicity of trinucleotide repeat can be uniquely tagged in separate reactions using the methods described and the individual reactions pooled to accomplish the standard set. The pool of synthetic standards can then be added to the amplified specimen and digested and sorted onto a standard pool of beads which will hybridize to both the unknown expanded and internal control fragments and to fragments comprising the standards (each with their respective internal controls). The expansion length of the unknown can then be assessed by comparing to the generated standard curve.

The compositions of the present invention may alternatively be comprised in a kit. In one embodiment, the compositions are comprised in a kit for diagnosing a trinucleotide expansion disease comprising a primer pair, each comprising a target specific sequence, a differentiating tag sequence 5' of the target specific sequence and a blocker between the target specific sequence and the differentiating tag sequence; a label; and a pair of capture complexes comprising an anti-tag sequence and a solid support. In a further embodiment, the kit further comprises a restriction enzyme which produces an expansion region fragment and an internal control fragment. In another embodiment, the compositions are comprised in a kit for screening the $(CGG)_n$ expansion region within the FMR1 gene comprising a primer pair, each comprising a target specific sequence, a differentiating tag sequence 5' of the target specific sequence and a blocker between the target specific sequence and the differentiating tag sequence; a label; and a pair of capture complexes comprising an anti-tag sequence and a solid support. In some embodiments, the primer pairs comprise SEQ ID NO: 1 and SEQ ID NO:2. In some embodiments, the kit further comprises a Taq1 restriction enzyme.

It is contemplated that any method or composition described herein can be implemented with respect to any other method or composition described herein.

The use of the term "or" in the claims is used to mean "and/or" unless explicitly indicated to refer to alternatives only or the alternatives are mutually exclusive, although the disclosure supports a definition that refers to only alternatives and "and/or."

Throughout this application, the term "about" is used to indicate that a value includes the standard deviation of error for the device or method being employed to determine the value.

Following long-standing patent law, the words "a" and "an," when used in conjunction with the word "comprising" in the claims or specification, denotes one or more, unless specifically noted.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 1—FMR1 amplified region. The FMR1 expansion $(CGG)_n$ trinucleotide repeat region is indicated in italicized underlined lettering. Amplification primers, (SEQ ID NO:3) are indicated by bold underlined lettering. A unique Taq1 restriction endonuclease site is shown in bold, italicized, underlined lettering.

FIG. 2—Tag and blocker location on the forward and reverse FMR1 expansion region primers. The amplification primers shown will generate an amplification product which spans the (CGG)$_n$ expansion region and encompasses a unique Taq1 restriction enzyme site. The primers include a target specific sequence (SEQ ID NOs: 1 and 2), a differentiating tag sequence, and a blocker moiety.

DESCRIPTION OF ILLUSTRATIVE EMBODIMENTS

A. Nucleic Acid Target Screening

The methods and compositions of the present invention allow for the evaluation of an expansion, contraction or deletion region in a nucleic acid sequence. For example, in one embodiment the present invention provides a method for detecting a nucleotide expansion, contraction or deletion region within a target nucleic acid sequence by (1) amplifying a target nucleic acid sequence with a primer pair, each primer comprising a target specific sequence, a differentiating tag sequence 5' of the target specific sequence and a blocker between the target specific sequence and the differentiating tag sequence to produce a dual-tagged amplification product; (2) labeling the dual-tagged amplification product; (3) digesting the dual-tagged amplification product with a restriction enzyme to produce a variation region fragment and an internal control fragment; (4) hybridizing the fragments to separate capture complexes comprising an anti-tag sequence and a solid support; (5) detecting a signal produced by the labels on the two fragments; and (6) comparing the intensity of the signal of the variation region fragment and the internal control fragment to detect the nucleotide expansion, contraction or deletion region.

This results in an evaluation method for mass screening and preliminary segregation of samples. The method of the present invention may be used, for example, in genetic screening for diseases such as Fragile X, Huntington's Disease (HD) or Spinobulbar Muscular Atrophy (SBMA). An issue that arises when attempting semi-quantification on arrays is the need for an internal control. If one were to simply infer that the signal intensity output is relative to the number of incorporated reporter molecules within the amplification product, one has no way of assessing if the value reflects the "quantity" of reporter molecules, the amplification product abundance or a combination of both. It can be expected that with regions which are 100% GC rich, amplification efficiency drops with increased length. Further, as the expansion increases the amplification product size increases, which results in overall lower median fluorescence intensity (MFI). This fact has been demonstrated across multiple samples with and without a tagged-primer and makes the use of external controls unsuitable. The MFI values for undigested amplification products are essentially without significance because the segregation to each respective capture complex can be erratic or bridging across two capture complexes can occur.

Figure 3:
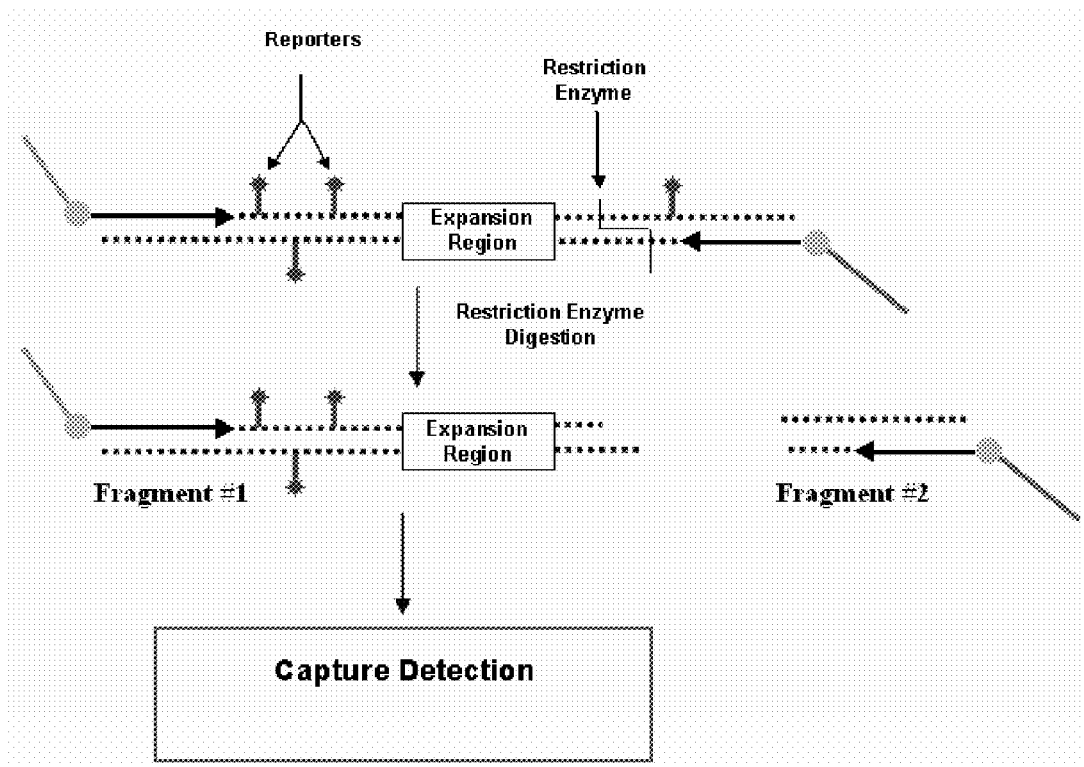
FIG. 3—Amplification and detection of FMR1 expansions using a dual-tagged amplification product. The FMR1 expansion region can be amplified with forward and reverse primers possessing a differentiating tag and blocker sequence. Following amplification, the amplification product is digested with Taq1 and the resulting fragments are captured onto Luminex beads or a similar anti-Tag array. The relative length of the expansion region is reflected in Fragment #1 while Fragment #2 represents an internal control.

The method of the current invention overcomes these obstacles by the digestion of a dual-tagged amplification product at a restriction enzyme site to generate a fragment whose length and hence number of labeled residues are constant. This fragment operates as an internal control, resolving the issues presented by the lower MFI of larger amplification products and the use of external controls. The length of the fragment encompassing the expansion, contraction or deletion region is variable. Under the current method, the effect of the abundance of the amplification product on the signal intensity is adjusted for by the invariable length of the internal control fragment. Capturing the variation region fragment and the internal control fragment on separate beads allows for novel methods of evaluation of the expansion, contraction or deletion region. In one embodiment, the MFI ratio between the MFI of the variation region fragment and the MFI of the internal control fragment can be compared against the MFI ratio obtained from known samples. For example, FIG. 3 provides a schematic representation of the amplification and detection of the FMR1 expansion region using a dual-tagged amplification product. The FMR1 expansion region can be amplified with forward and reverse primers possessing a differentiating tag and a blocker sequence. Following amplification, the amplification product is digested with a Taq1 restriction enzyme and the resulting fragments are captured onto Luminex beads or a similar anti-tag array. The relative length of the expansion region is reflected in Fragment #1 while Fragment #2 represents an internal control.

In certain embodiments, the present invention is used in conjunction with Luminex® xMAP® technology. The Luminex technology allows the quantization of nucleic acid products immobilized on distinct populations (sets) of fluorescently encoded beads. These individual populations (sets) can represent individual detection sequences and the magnitude of variation on each set can be detected individually. For example, the variation region fragment of the current invention is immobilized on one set through the hybridization of the differentiating tag sequence with its anti-tag complement, and the internal control fragment is immobilized on a second set. This allows separate detection of the two fragments. The reporter molecule signals the extent of the variation by attaching to the molecules on the beads. As both the beads and the reporter molecules are labeled, digital signal processing allows the translation of signals into real-time, quantitative data for each reaction. The Luminex technology is described, for example, in U.S. Pat. Nos. 5,736,330, 5,981,180, and 6,057,107, all of which are specifically incorporated by reference.

B. Amplification and Digestion

Each primer includes a gene specific sequence, a differentiating tag sequence, and a blocker. These primers will generate an amplification product that spans the expansion, contraction or deletion region and encompass a unique restriction enzyme site. As an illustration, FIG. 2 demonstrates the tagging and blocker location of the forward and reverse amplification primers designed to bracket the FMR1 expansion region.

Each amplification primer possesses a differentiating tag sequence. The tag sequences are the complement of the anti-tag sequence of two capture complexes. Specific hybridization between each tag sequence and each anti-tag sequence allows for the capture of the amplified target nucleic acid sequence by the appropriate capture complex. As mentioned above, a number of tag and tag complement sequences are known in the art and may be used in the present invention. For example, U.S. Pat. No. 7,226,737 describes a set of 210 non-cross hybridizing tags and anti-tags. In addition, U.S. Published Application No. 2005/0191625 discloses a family of 1168 tag sequences with a demonstrated ability to correctly hybridize to their complementary sequences with minimal cross hybridization to other tag sequences or their complements. A number of approaches have been developed that involve the use of oligonucleotide tags attached to a solid support that can be used to specifically hybridize to the tag complements that are coupled to primers, probe sequences, target sequences, etc. The proper selection of non-cross hybridizing tag and anti-tag sequences is useful in assays, particularly assays in a highly parallel hybridization environment, that require stringent non-cross hybridizing behavior.

A blocker moiety is positioned between the tag and gene specific regions. A blocker moiety refers to any moiety that when linked (e.g., covalently linked) between a first nucleotide sequence and a second nucleotide sequence is effective to inhibit and preferably prevent extension, during second strand synthesis, through either the first or second nucleotide sequence templates.

Once generated, the dual tagged amplification product is digested with a restriction endonuclease to generate two fragments which are differentially tagged. The restriction enzyme is selected to digest the dual tagged amplification product such that one fragment contains the expansion, contraction or deletion region and a second fragment contains an internal control. The length of the fragment containing the variation region will vary with the size of the expansion, contraction or deletion, while the length of the internal control fragment will not vary. Restriction enzyme digestion refers to catalytic cleavage of a nucleic acid molecule with an enzyme that functions only at specific locations in a nucleic acid molecule. Many of these restriction enzymes are commercially available. Use of such enzymes is widely understood by those of skill in the art, and as such a person of ordinary skill in the art could readily identify an appropriate restriction enzyme for a target sequence. For example, the restriction digestion process can be performed with FastDigest restriction enzymes (i.e., Fermentas Life Sciences).

It is also possible to omit the blocker moiety from the primer. In this case, steps are taken to permit the hybridization of the tag sequence with the anti-tag sequence subsequent to restriction enzyme digestion. The double-stranded amplification product which contains an anti-tag/tag region at each end is then denatured to render the DNA strands single stranded prior to hybridization to the appropriate anti-tag coupled to the solid substrate. As an alternative to denaturation, enzymatic treatment of the double-stranded amplification product may be used to eliminate the anti-tag containing strands.

C. Nucleic Acids

1. Preparation of Nucleic Acids

The tag sequences, anti-tag sequences, and primers disclosed herein may be prepared by any technique known to one of ordinary skill in the art, such as for example, chemical synthesis, enzymatic production, or biological production. Non-limiting examples of a synthetic nucleic acid (e.g., a synthetic oligonucleotide), include a nucleic acid made by in vitro chemical synthesis using phosphotriester, phosphite or phosphoramidite chemistry and solid phase techniques such as described in EP 266032, incorporated herein by reference, or via deoxynucleoside H-phosphonate intermediates as described by Froehler et al. (1986) and U.S. Pat. No. 5,705,629, each incorporated herein by reference. Various different mechanisms of oligonucleotide synthesis have been disclosed in for example, U.S. Pat. Nos. 4,659,774, 4,816,571, 5,141,813, 5,264,566, 4,959,463, 5,428,148, 5,554,744, 5,574,146, 5,602,244, each of which is incorporated herein by reference.

A non-limiting example of an enzymatically produced nucleic acid include one produced by enzymes in amplification reactions such as PCR™ (see for example, U.S. Pat. No. 4,683,202 and U.S. Pat. No. 4,682,195, each incorporated herein by reference), or the synthesis of an oligonucleotide described in U.S. Pat. No. 5,645,897, incorporated herein by reference. A non-limiting example of a biologically produced nucleic acid includes a recombinant nucleic acid produced (i.e., replicated) in a living cell, such as a recombinant DNA vector replicated in bacteria (see for example, Sambrook et al. (2001), incorporated herein by reference).

Nucleic acids used as a template for amplification may be isolated from cells, tissues or other samples according to standard methodologies (Sambrook et al., 2001). In certain embodiments, analysis is performed on whole cell or tissue homogenates or biological fluid samples without substantial purification of the template nucleic acid. The nucleic acid may be genomic DNA or fractionated or whole cell RNA. Where RNA is used, it may be desired to first convert the RNA to a complementary DNA.

The term "primer," as used herein, is meant to encompass any nucleic acid that is capable of priming the synthesis of a nascent nucleic acid in a template-dependent process. Typically, primers are oligonucleotides from ten to twenty and/or thirty base pairs in length, but longer sequences can be employed. Primers may be provided in double-stranded and/or single-stranded form, although the single-stranded form is preferred.

Depending upon the desired application, high stringency hybridization conditions may be selected that will only allow hybridization to sequences that are completely complementary to the primers. In other embodiments, hybridization may occur under reduced stringency to allow for amplification of nucleic acids containing one or more mismatches with the primer sequences. Once hybridized, the template-primer complex is contacted with one or more enzymes that facilitate template-dependent nucleic acid synthesis. Multiple rounds of amplification, also referred to as "cycles," are conducted until a sufficient amount of amplification product is produced.

A reverse transcriptase PCR™ amplification procedure may be performed to reverse transcribe mRNA into cDNA. Methods of RT-PCR are well known in the art (see Sambrook et al, 2001). Alternative methods for reverse transcription utilize thermostable DNA polymerases. These methods are described in WO 90/07641. Polymerase chain reaction methodologies are well known in the art. Representative methods of RT-PCR are described in U.S. Pat. No. 5,882,864.

Another method for amplification is ligase chain reaction ("LCR"), disclosed in European Application No. 320 308, incorporated herein by reference in its entirety. U.S. Pat. No. 4,883,750 describes a method similar to LCR for binding probe pairs to a target sequence. A method based on PCR™ and oligonucleotide ligase assay (OLA), disclosed in U.S. Pat. No. 5,912,148, may also be used.

Alternative methods for amplification of nucleic acid sequences that may be used in the practice of certain aspects of the present invention are disclosed in U.S. Pat. Nos. 5,843,650, 5,846,709, 5,846,783, 5,849,546, 5,849,497, 5,849,547, 5,858,652, 5,866,366, 5,916,776, 5,922,574, 5,928,905, 5,928,906, 5,932,451, 5,935,825, 5,939,291 and 5,942,391, GB Application No. 2 202 328, and in PCT Application No. PCT/US89/01025, each of which is incorporated herein by reference in its entirety.

Qbeta Replicase, described in PCT Application No. PCT/US87/00880, may also be used as an amplification method in the present invention. In this method, a replicative sequence of RNA that has a region complementary to that of a target is added to a sample in the presence of an RNA polymerase. The polymerase will copy the replicative sequence, which may then be detected.

An isothermal amplification method, in which restriction endonucleases and ligases are used to achieve the amplification of target molecules that contain nucleotide 5'-[alpha-thio]-triphosphates in one strand of a restriction site may also be useful in the amplification of nucleic acids in the present invention (Walker et al., 1992). Strand Displacement Amplification (SDA), disclosed in U.S. Pat. No. 5,916,779, is another method of carrying out isothermal amplification of nucleic acids, which involves multiple rounds of strand displacement and synthesis, i.e., nick translation.

Other nucleic acid amplification procedures include transcription-based amplification systems (TAS), including nucleic acid sequence based amplification (NASBA) and 3SR (Kwoh et al., 1989; Gingeras et al., PCT Application WO 88/10315, incorporated herein by reference in their entirety). European Application No. 329 822 disclose a nucleic acid amplification process involving cyclically synthesizing single-stranded RNA ("ssRNA"), ssDNA, and double-stranded DNA (dsDNA).

PCT Application WO 89/06700 (incorporated herein by reference in its entirety) disclose a nucleic acid sequence amplification scheme based on the hybridization of a promoter region/primer sequence to a target single-stranded DNA ("ssDNA") followed by transcription of many RNA copies of the sequence. This scheme is not cyclic, i.e., new templates are not produced from the resultant RNA transcripts. Other amplification methods include "race" and "one-sided PCR™" (Frohman, 1990; Ohara et al., 1989).

Amplification products may be visualized. If the amplification products are integrally labeled with radio- or fluorescent-labeled nucleotides, the separated amplification products can be exposed to x-ray film or visualized under the appropriate excitatory spectra. In another approach, a labeled nucleic acid probe is brought into contact with the amplified marker sequence, following separation of the amplification products. The probe may be conjugated to, for example, a chromophore, fluorophore, radiolabel, or conjugated to a binding partner, such as an antibody or biotin.

Various nucleic acid detection methods known in the art are disclosed in U.S. Pat. Nos. 5,840,873, 5,843,640, 5,843,651, 5,846,708, 5,846,717, 5,846,726, 5,846,729, 5,849,487, 5,853,990, 5,853,992, 5,853,993, 5,856,092, 5,861,244, 5,863,732, 5,863,753, 5,866,331, 5,905,024, 5,910,407, 5,912,124, 5,912,145, 5,919,630, 5,925,517, 5,928,862, 5,928,869, 5,929,227, 5,932,413 and 5,935,791, each of which is incorporated herein by reference.

2. Nucleic Acid Analogs

A nucleic acid sequence may comprise, or be composed entirely of, an analog of a naturally occurring nucleotide. As used herein an "analog" refers to a molecule that may or may not structurally resemble a naturally occurring molecule or moiety, but possesses similar functions.

Nucleotide analogs are well known in the art. A non-limiting example is a "peptide nucleic acid," also known as a "PNA," "peptide-based nucleic acid analog," or "PENAM," described in U.S. Pat. Nos. 5,786,461, 5,891,625, 5,773,571, 5,766,855, 5,736,336, 5,719,262, 5,714,331, 5,539,082, and WO 92/20702, each of which is incorporated herein by reference. Peptide nucleic acids generally have enhanced sequence specificity, binding properties, and resistance to enzymatic degradation in comparison to molecules such as DNA and RNA (Egholm et al., 1993; PCT/EP/01219). A peptide nucleic acid generally comprises one or more nucleotides or nucleosides that comprise a nucleobase moiety, a nucleobase linker moiety that is not a 5-carbon sugar, and/or a backbone moiety that is not a phosphate backbone moiety. Examples of nucleobase linker moieties described for PNAs include aza nitrogen atoms, amido and/or ureido tethers (see for example, U.S. Pat. No. 5,539,082). Examples of backbone moieties described for PNAs include an aminoethylglycine, polyamide, polyethyl, polythioamide, polysulfinamide or polysulfonamide backbone moiety.

Another non-limiting example is a locked nucleic acid or "LNA." An LNA monomer is a bi-cyclic compound that is structurally similar to RNA nucleosides. LNAs have a furanose conformation that is restricted by a methylene linker that connects the 2'-O position to the 4'-C position, as described in Koshkin et al., (1998a, 1998b) and Wahlestedt et al. (2000).

Yet another non-limiting example is a "polyether nucleic acid," described in U.S. Pat. No. 5,908,845, incorporated herein by reference. In a polyether nucleic acid, one or more nucleobases are linked to chiral carbon atoms in a polyether backbone.

3. Hybridization

Sequence-specific nucleic acid hybridization assays are used for the detection of specific genetic sequences as indicators of genetic anomalies, mutations, and disease propensity. In addition, they are used for the detection of various biological agents and infectious pathogens. As used herein, "hybridization," "hybridizes" or "capable of hybridizing" is understood to mean the forming of a double or triple stranded molecule or a molecule with partial double or triple stranded nature. The term "anneal" as used herein is synonymous with "hybridize." The term "hybridization," "hybridizes" or "capable of hybridizing" encompasses the terms "stringent conditions" or "high stringency" and the terms "low stringency" or "low stringency conditions."

As used herein "stringent conditions" or "high stringency" are those conditions that allow hybridization between or within one or more nucleic acid strands containing complementary sequences, but preclude hybridization of non-complementary sequences. Such conditions are well known to those of ordinary skill in the art, and are preferred for applications requiring high selectivity. Stringent conditions may comprise low salt and/or high temperature conditions, such as provided by about 0.02 M to about 0.15 M NaCl at temperatures of about 50° C. to about 70° C. It is understood that the temperature and ionic strength of a desired stringency are determined in part by the length of the particular nucleic acids, the length and nucleobase content of the target sequences, the charge composition of the nucleic acids, and to the presence or concentration of formamide, tetramethylammonium chloride or other solvents in a hybridization mixture.

It is also understood that these ranges, compositions and conditions for hybridization are mentioned by way of non-limiting examples only, and that the desired stringency for a particular hybridization reaction is often determined empirically by comparison to one or more positive or negative controls. Non-limiting examples of low stringency conditions include hybridization performed at about 0.15 M to about 0.9 M NaCl at a temperature range of about 20° C. to about 50° C.

Of course, it is within the skill of one in the art to further modify the low or high stringency conditions to suite a particular application.

D. Detection of Nucleic Acids

1. Labels

Figure 4:
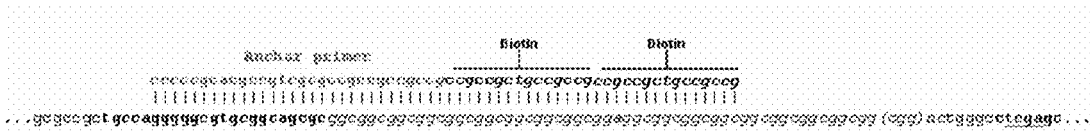
FIG. 4—Alternative labeling scheme for the evaluation of expansion regions. An anchor and biotinylated-expansion region specific oligomers are hybridized to the amplification product following digestion. The biotinylated oligomers can provide uniform spacing between labels, which can yield greater signal uniformity without the need for directly incorporating biotin-nucleotides during synthesis (SEQ ID NOS:4 and 5).

To detect nucleic acids, it will be advantageous to employ nucleic acids in combination with an appropriate detection means. Recognition moieties incorporated into primers, incorporated into the amplified product during amplification, or attached to probes are useful in the identification of nucleic acid molecules. For example, amplification may occur in the presence of a reporter molecule which labels the dual-tagged amplification product. FIG. 3 illustrates the amplification product labeled by direct labeling. Alternatively, the amplification product may be denatured and the fragments may hybridize to short labeled fragments that are complementary to the variation region. In this embodiment, the labeled oligomers can provide uniform spacing between labels, which can yield greater signal uniformity without the need for directly incorporating labeled-nucleotides during synthesis. FIG. 4 provides an illustration of this alternative detection scheme for its use screening the expansion region of the FRM1 gene.

A number of different labels may be used for this purpose such as fluorophores, chromophores, radiophores, enzymatic tags, antibodies, chemiluminescence, electroluminescence, affinity labels, etc. One of skill in the art will recognize that these and other labels not mentioned herein can be used with success in this invention. Examples of affinity labels include, but are not limited to the following: an antibody, an antibody fragment, a receptor protein, a hormone, biotin, DNP, or any polypeptide/protein molecule that binds to an affinity label.

Examples of enzyme tags include enzymes such as urease, alkaline phosphatase or peroxidase to mention a few. Colorimetric indicator substrates can be employed to provide a detection means visible to the human eye or spectrophotometrically, to identify specific hybridization with complementary nucleic acid-containing samples. All of these examples are generally known in the art and the skilled artisan will recognize that the invention is not limited to the examples described above.

Examples of fluorophores include, a red fluorescent squarine dye such as 2,4-Bis[1,3,3-trimethyl-2-indolinylidenemethyl]cyclobutenediylium-1,3-dioxolate, an infrared dye such as 2,4 Bis[3,3-dimethyl-2-(1H-benz[e]indolinylidenemethyl)]cyclobutenediylium-1,3-dioxolate, or an orange fluorescent squarine dye such as 2,4-Bis[3,5-dimethyl-2-pyrrolyl]cyclobutenediylium-1,3-diololate. Additional non-limiting examples of fluorophores include quantum dots, Alexa Fluor® dyes, AMCA, BODIPY® 630/650, BODIPY® 650/665, BODIPY®-FL, BODIPY®-R6G, BODIPY®-TMR, BODIPY®-TRX, Cascade Blue®, CyDye™, including but not limited to Cy2™, Cy3™, and Cy5™, a DNA intercalating dye, 6-FAM™, Fluorescein, HEX™, 6-JOE, Oregon Green® 488, Oregon Green® 500, Oregon Green® 514, Pacific Blue™, REG, phycobilliproteins including, but not limited to, phycoerythrin and allophycocyanin, Rhodamine Green™, Rhodamine Red™, ROX™, TAMRA™, TET™, Tetramethylrhodamine, or Texas Red®.

2. Gene Chips and Microarrays

The capture complexes of the present invention may comprise a gene chip or microarray. Arrays and gene chip technology provide a means of rapidly screening a large number of nucleic acid samples for their ability to hybridize to a variety of single stranded oligonucleotide probes immobilized on a solid substrate. The technology capitalizes on the complementary binding properties of single stranded DNA to screen DNA samples by hybridization (Pease et al 1994; Fodor et al. 1991). Basically, an array or gene chip consists of a solid substrate upon which an array of single stranded DNA or RNA molecules have been attached. For screening, the chip or array is contacted with a single stranded DNA or RNA sample, which is allowed to hybridize under stringent conditions. The chip or array is then scanned to determine which probes have hybridized. In the present invention, anti-tags are located on the chip or array and hybridize to the tags.

The ability to directly synthesize on or attach polynucleotide probes to solid substrates is well known in the art. See U.S. Pat. Nos. 5,837,832 and 5,837,860, both of which are expressly incorporated by reference. A variety of methods have been utilized to either permanently or removably attach the probes to the substrate. Exemplary methods include: the immobilization of biotinylated nucleic acid molecules to avidin/streptavidin coated supports (Holmstrom, 1993), the direct covalent attachment of short, 5'-phosphorylated primers to chemically modified polystyrene plates (Rasmussen et al., 1991), or the precoating of the polystyrene or glass solid phases with poly-L-Lys or poly L-Lys, Phe, followed by the covalent attachment of either amino- or sulfhydryl-modified oligonucleotides using bi-functional crosslinking reagents (Running et al., 1990; Newton et al., 1993). When immobilized onto a substrate, the probes are stabilized and therefore may be used repeatedly. In general terms, hybridization is performed on an immobilized nucleic acid target or a probe molecule that is attached to a solid surface such as nitrocellulose, nylon membrane or glass. Numerous other matrix materials may be used, including reinforced nitrocellulose membrane, activated quartz, activated glass, polyvinylidene difluoride (PVDF) membrane, polystyrene substrates, polyacrylamide-based substrate, other polymers such as poly(vinyl chloride), poly(methyl methacrylate), poly(dimethyl siloxane), photopolymers (which contain photoreactive species such as nitrenes, carbenes and ketyl radicals capable of forming covalent links with target molecules.

3. Luminex xMAP Technology

In certain embodiments, the present invention is used in conjunction with Luminex® xMAP® technology. The Luminex technology allows the quantitation of nucleic acid products immobilized on fluorescently encoded microspheres. By dyeing microspheres with 10 different intensities of each of two spectrally distinct fluorochromes, 100 fluorescently distinct populations of microspheres are produced. These individual populations (sets) can represent individual detection sequences. For example, the variation region fragment of the current invention may be immobilized on one set of microspheres through the hybridization of the differentiating tag sequence with its anti-tag complement, and the internal control fragment may be immobilized on a second set of microspheres. This allows separate detection of the two fragments. The magnitude of the variation between the variation region fragment and the internal control fragment is measured using the reporter that was incorporated into or otherwise attached to the amplification product as discussed above. The reporter used to label the amplification product may be, for example, a fluorophore that is spectrally distinct from the two fluorophores used to dye the microspheres. As the microspheres, the variation region fragments, and the internal control fragments are labeled, digital signal processing allows the translation of signals into real-time, seimquantitative or quantitative data for each reaction. The Luminex technology is described, for example, in U.S. Pat.

Nos. 5,736,330, 5,981,180, and 6,057,107, all of which are specifically incorporated by reference.

4. Flow Cytometry

Flow cytometry is a useful tool in the analysis of biomolecules. In the context of the present invention, flow cytometry is particularly useful in the analysis of microsphere based assays, such as the Luminex xMAP® system. Flow cytometry involves the separation of cells or other particles, such as microspheres, in a liquid sample. Generally, the purpose of flow cytometry is to analyze the separated particles for one or more characteristics. The basic steps of flow cytometry involve the direction of a fluid sample through an apparatus such that a liquid stream passes through a sensing region. The particles should pass one at a time by the sensor and are categorized based on size, refraction, light scattering, opacity, roughness, shape, fluorescence, etc.

In the context of the Luminex xMAP system, internal dyes in the microspheres are detected by flow cytometry and used to identify the specific nucleic acid sequence to which a microsphere is coupled. The label on the variation region fragment is detected by flow cytometry and used to evaluate the size of the expansion, contraction or deletion region. The label on the internal control fragment is also detected by flow cytometry and used to determine an internal control signal level.

Methods of flow cytometry are well know in the art and are described, for example, in U.S. Pat. Nos. 5,981,180, 4,284,412; 4,989,977; 4,498,766; 5,478,722; 4,857,451; 4,774,189; 4,767,206; 4,714,682; 5,160,974; and 4,661,913, all of which are specifically incorporated by reference.

5. Bead Arrays

Microsphere based assays may also be analyzed on bead array platforms. In general, bead array platforms image beads and analytes distributed on a substantially planar array. In this way, imaging of bead arrays is similar to the gene chips discussed above. However, in contrast to gene chips where the analyte is identified by its spatial position on the array, bead arrays typically identify the analyte by the encoded microsphere to which it is bound. Examples of commercially available bead array systems include Illumina's BeadXpress™ Reader and BeadStation 500™.

6. Tag Sequences

As mentioned above, various aspects of the present invention use complementary tag sequences (i.e., tags and anti-tags) in the primers and capture molecules. A number of approaches have been developed that involve the use of oligonucleotide tags attached to a solid support that can be used to specifically hybridize to the tag complements that are coupled to primers, probe sequences, target sequences, etc. The proper selection of non-hybridizing tag and anti-tag sequences is useful in assays, particularly assays in a highly parallel hybridization environment, that require stringent non-cross hybridizing behavior.

Certain thermodynamic properties of forming nucleic acid hybrids are considered in the design of tag and anti-tag sequences. The temperature at which oligonucleotides form duplexes with their complementary sequences known as the $T_m$ (the temperature at which 50% of the nucleic acid duplex is dissociated) varies according to a number of sequence dependent properties including the hydrogen bonding energies of the canonical pairs A-T and G-C (reflected in GC or base composition), stacking free energy and, to a lesser extent, nearest neighbor interactions. These energies vary widely among oligonucleotides that are typically used in hybridization assays. For example, hybridization of two probe sequences composed of 24 nucleotides, one with a 40% GC content and the other with a 60% GC content, with its complementary target under standard conditions theoretically may have a 10° C. difference in melting temperature (Mueller et al., 1993). Problems in hybridization occur when the hybrids are allowed to form under hybridization conditions that include a single hybridization temperature that is not optimal for correct hybridization of all oligonucleotide sequences of a set. Mismatch hybridization of non-complementary probes can occur forming duplexes with measurable mismatch stability (Santalucia et al., 1999). Mismatching of duplexes in a particular set of oligonucleotides can occur under hybridization conditions where the mismatch results in a decrease in duplex stability that results in a higher $T_m$ than the least stable correct duplex of that particular set. For example, if hybridization is carried out under conditions that favor the AT-rich perfect match duplex sequence, the possibility exists for hybridizing a GC-rich duplex sequence that contains a mismatched base having a melting temperature that is still above the correctly formed AT-rich duplex. Therefore, design of families of oligonucleotide sequences that can be used in multiplexed hybridization reactions must include consideration for the thermodynamic properties of oligonucleotides and duplex formation that will reduce or eliminate cross hybridization behavior within the designed oligonucleotide set.

There are a number of different approaches for selecting tag and anti-tag sequences for use in multiplexed hybridization assays. The selection of sequences that can be used as zip codes or tags in an addressable array has been described in the patent literature in an approach taken by Brenner and coworkers (U.S. Pat. No. 5,654,413, incorporated herein by reference). Chetverin et al. (WO 93/17126, U.S. Pat. Nos. 6,103,463 and 6,322,971, incorporated herein by reference) discloses sectioned, binary oligonucleotide arrays to sort and survey nucleic acids. These arrays have a constant nucleotide sequence attached to an adjacent variable nucleotide sequence, both bound to a solid support by a covalent linking moiety. Parameters used in the design of tags based on subunits are discussed in Barany et al. (WO 9731256, incorporated herein by reference). A multiplex sequencing method has been described in U.S. Pat. No. 4,942,124, incorporated herein by reference. This method uses at least two vectors that differ from each other at a tag sequence.

U.S. Pat. No. 7,226,737, incorporated herein by reference, describes a set of 210 non-cross hybridizing tags and anti-tags. U.S. Published Application No. 2005/0191625, incorporated herein by reference, discloses a family of 1168 tag sequences with a demonstrated ability to correctly hybridize to their complementary sequences with minimal cross hybridization.

A population of oligonucleotide tag or anti-tag sequences may be conjugated to a population of primers or other polynucleotide sequences in several different ways including, but not limited to, direct chemical synthesis, chemical coupling, ligation, amplification, and the like. Tags that have been synthesized with primer sequences can be used for enzymatic extension of the primer on the target for example in PCR amplification. A population of oligonucleotide tag or anti-tag sequences may be conjugated to a solid support by, for example, surface chemistries on the surface of the support.

7. Blocker Moieties

As discussed above, each primer of a primer pair used in an amplification reaction comprises a differentiating tag sequence. Following the initial extension of the primers, the tagged extension product could potentially serve as a template for the other primer of the primer pair. It would be undesirable, however, for the extension on such a template to proceed through the tag region as this would interfere with the hybridization of the tag sequence with the anti-tag sequence of the capture complex. Accordingly, a blocker is positioned between the target specific sequence and the tag sequence of the primer. Blocker moieties prevent the polymerase from extending into the tag sequence region, which allows the tag sequence to remain single-stranded during amplification and therefore free to hybridize to its complementary anti-tag sequence in the capture complex.

A blocker moiety refers to any moiety that when linked (e.g., covalently linked) between a first nucleotide sequence and a second nucleotide sequence is effective to inhibit and preferably prevent extension of either the first or second nucleotide sequence but not both the first and second nucleotide sequence. There are a number of molecules that may be used as blocker moieties. Non-limiting examples of blocker moieties include C6-20 straight chain alkylenes and iSp18 (which is an 18-atom hexa-ethyleneglycol). Blocker moieties may include, for example, at least one deoxy ribofuranosyl naphthalene or ribofuranosyl naphthalene moiety, which may be linked to the adjacent nucleotides via a 3'-furanosyl linkage or preferably via a 2'-furanosyl linkage. A blocker moiety may be an oligonucleotide sequence that is in the opposite orientation as the target specific sequence. Accordingly, in certain aspects of the invention a primer's tag sequence may be both the tag and the blocker. Various blocker moieties and their use are described in U.S. Pat. No. 5,525,494, which is incorporated herein by reference.

It is also possible to omit the blocker moiety from the primer. In this case, steps are taken to permit the hybridization of the tag sequence with the anti-tag sequence subsequent to restriction enzyme digestion. The double-stranded amplification product which contains an anti-tag/tag region at each end is then denatured to render the DNA strands single stranded prior to hybridization to the appropriate anti-tag coupled to the solid substrate. As an alternative to denaturation, enzymatic treatment of the double-stranded amplification product may be used to eliminate the anti-tag containing strands.

E. Comparing Intensities of Signals

As mentioned above, the intensities of the signals of the expansion, contraction or deletion region fragment and the internal control fragment are compared to evaluate the nucleotide variation region. Following digestion, the expansion region fragment and the internal control fragment each remain labeled with the reporter molecule. The variation region fragment and the internal control fragment are then hybridized to separate anti-tag sequences via their respective tag sequences. The anti-tag sequences are immobilized on a solid support. The intensities of the signal of the expansion region fragment and the internal control fragment will reflect the number of labeled residues found on each fragment. The expansion region fragment will have an amount of reporter molecules that is related to the length of the expansion region, while the internal control fragment will have a constant number of reporter molecules. The effect of the abundance of the amplification product on the signal intensity is adjusted for by the invariable length of the internal control fragment.

The evaluation may be quantitative or semi-quantitative. In many applications, a semi-quantitative evaluation is sufficient to identify which samples contain regions that contain an abnormal variation region. In one embodiment, a semi-quantitative evaluation may be performed by direct comparison of the median fluorescence intensity (MFI) of the variation region fragment to the MFI of the internal control fragment. For example, a sample may be semi-quantitatively screened for an expanded trinucleotide repeat region of the FRM1 gene. A comparison may made between the ratio achieved with samples having known numbers of repeats and the ratio achieved with a target sample. It is known that the expansion size of a normal FMR1 gene contains between 5 and 44 repeats of the CGG trinucleotide, while a person affected with Fragile X contains over 200 repeats.

Alternatively, the method could provide a quantitative evaluation of the expansion, contraction or deletion in a nucleic acid sequence. In this instance, a series of standards comprising a collection of trinucleotide expansions can be run along side the query sample to quantitatively determine the repeat length of the unknown. The standards can be generated from synthetic material so that the necessary characteristics of the authentic trinucleotide repeat are maintained. Each periodicity of trinucleotide repeat can be uniquely tagged in separate reactions using the methods described and the individual reactions pooled to accomplish the standard set. The pool of synthetic standards can then be added to the amplified specimen and digested and sorted onto a standard pool of beads which will hybridize to both the unknown expanded and internal control fragments and to fragments comprising the standards (each with their respective internal controls). The expansion length of the unknown can then be assessed by comparing to the generated standard curve.

F. Trinucleotide Expansion Diseases on the X Chromosome

The methods and compositions of the present invention are well-suited for the evaluation of a nucleotide expansion, contraction or deletion on the X chromosome. In particular, the methods and compositions of the present invention may be used for screening trinucleotide repeat regions on the X chromosome. Several diseases involve trinucleotide expansions on the X chromosome. These diseases include Fragile X syndrome, Fragile XE mental retardation, and spinobulbar muscular atrophy.

Fragile-X is associated with a CGG trinucleotide repeat region of the FMR1 gene on the X chromosome. Symptoms of the disease may include mental impairment, ranging from learning disabilities to mental retardation, attention deficit and hyperactivity, anxiety and unstable mood, autistic behaviors, long face, large ears, flat feet and hyperextensible joints, especially fingers. About 25% of people affected with Fragile-X also experience epilepsy, and males are typically more severely affected than females. Emotional and behavioral problems are common in both sexes, while mental retardation more severely affects males. The majority of affected males have mental retardation. In contrast, only one-third to one-half of females have significant intellectual impairment, with the rest having either normal IQ or learning disabilities. Approximately 20% of males with Fragile-X meet the full criteria for autism. Most males and some females have some symptoms of autism, but many tend to be very social and interested in other people. A normal FMR1 gene typically contains between about 5 and 44 CGG repeats, whereas in people with Fragile X the FMR1 typically has over 200 CGG repeats. Mothers of individuals affected by Fragile X syndrome have been found to have a pre-expansion of about 60 and 200 CGG repeats. The human FMR1 gene is deposited as GenBank Accession Number NM_002024.

Fragile XE mental retardation (FRAXE) is a rare, non-specific form of mental handicap and involves the GCC trinucleotide repeat in FMR2 on the X chromosome. Common symptoms of FRAXE include mild mental retardation, learning deficits, and possible developmental delays. A normal FMP2 gene typically contains between 6 and 35 copies of GCC, while people with FRAXE have over 200 repeats. The human FMR2 gene is deposited as GenBank Accession Number AH008014.

Spinobulbar muscular atrophy, also known as Kennedy syndrome, involves the CAG trinucleotide repeat in the androgen receptor gene on the X chromosome and is a rare disease affecting the nerves and muscles. This condition is a form of motor neuron disease, occurs in adults, and causes progressive muscle weakness and wasting of the voluntary muscles. Symptoms may include facial weakness, tongue weakness, disphagia, dysarthria, and gynecomastia. The disease can cause men to become infertile due to unresponsiveness to androgen, a male hormone. A normal androgen receptor gene typically contains between 9 and 36 copies of CAG, whereas a person having the disease typically has between 38 and 62 copies. The human Androgen receptor gene is deposited as GenBank Accession Number NM 000044.

G. Kits

Any of the compositions described herein may be comprised in a kit. In one embodiment, the compositions are comprised in a kit for diagnosing a trinucleotide expansion disease comprising a primer pair, each comprising a target specific sequence, a differentiating tag sequence 5' of the target specific sequence and a blocker between the target specific sequence and the differentiating tag sequence; a label; and a pair of capture complexes comprising an anti-tag sequence and a solid support. Alternatively, the blocker may be omitted from the primers in the kit. In a further embodiment, the kit further comprises a restriction enzyme which produces an expansion region fragment and an internal control fragment. In another embodiment, the compositions are comprised in a kit for screening the $(CGG)_n$ expansion region within the FMR1 gene comprising a primer pair, each comprising a target specific sequence, a differentiating tag sequence 5' of the target specific sequence and a blocker between the target specific sequence and the differentiating tag sequence; a label; and a pair of capture complexes comprising an anti-tag sequence and a solid support. Alternatively, the blocker may be omitted from the primers in the kit. In some embodiments, the primer pairs comprise SEQ ID NO:1 and SEQ ID NO:2. In some embodiments, the kit further comprises a Taq1 restriction enzyme.

The kits may comprise suitably aliquoted nucleic acid compositions of the present invention, whether labeled or unlabeled, as may be used to isolate, separate, detect, or amplify a targeted nucleic acid. The components of the kits may be packaged either in aqueous media or in lyophilized form. The container means of the kits will generally include at least one vial, test tube, flask, bottle, syringe or other container means, into which a component may be placed, and preferably, suitably aliquoted. Where there is more than one component in the kit, the kit also will generally contain a second, third or other additional containers into which the additional components may be separately placed. However, various combinations of components may be comprised in a vial. The kits of the present invention also will typically include a means for containing the primers, labels, capture complexes and any other reagent containers in close confinement for commercial sale. Such containers may include cardboard or injection or blow-molded plastic containers into which the desired vials, bottles, etc. are retained.

When the components of the kit are provided in one or more liquid solutions, the liquid solution may be an aqueous solution, with a sterile aqueous solution being particularly preferred.

However, the components of the kit may be provided as dried powder(s). When reagents and/or components are provided as a dry powder, the powder can be reconstituted by the addition of a suitable solvent. It is envisioned that the solvent may also be provided in another container means.

A kit may also include instructions for employing the kit components. Instructions may include variations that can be implemented.

H. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

A screening method was developed for investigating an expansion variation within the FMR1 gene. Generally, high resolution electrophoretic methods, including sequencing, are used to quantify the number of $(CGG)_n$ repeats present. Although very accurate, these methods are slow, expensive and cumbersome for general screening. A semi-quantitative test as described below may be used for mass screening and preliminary segregation of samples.

Three samples were selected that contained a known trinucleotide repeat size. The samples were selected from human males and included a $(CGG)_n$ repeat size of 20, 80-85 and 117. Samples NA06891 and NA06892 were obtained from CORIELL CELL REPOSITORIES. With sample NA06892, which contained a repeat size of 80-85, the reference method used to assess the repeat length for the characterized sample was gel based, which only enables an approximate estimation of the repeat length. Each sample was amplified using primers comprising SEQ ID NO: 1 and SEQ ID NO:2 (1 µM) in the presence of 100 µM Biotin-dCTP, 100 µM dCTP, 200 µM each of dATP, dTTP and deAza-dGTP; 1.25 M Betaine; 1×TaKaRa PCR buffer and 1 U of TaKaRa DNA Polymerase. If necessary, the unincorporated nucleotides can be removed by sephadex-G50 chromatography. FIG. 2 illustrates the primers used for the amplification of the samples. Following amplification, the amplification product was digested with a Taq1 restriction endonuclease in a reaction composed of 100 mM NaCl, 50 mM Tris-HCl (Ph7.0 at 25° C.), 10 mM $MgCl_2$, 1 mM dithiothreitol, 100 µg/mL BSA and 20 U Taq 1 in a final volume of 15 µL to generate two fragments. FIG. 3 demonstrates the generation of the expansion region fragment and the internal control fragment. These fragments were hybridized to separate anti-tag sequences via their respective tag sequences immobilized on two sets of Luminex beads.

Detection of the labeled, double-stranded product was carried out on the Luminex instrument. 45 uL of appropriately anti-tag coupled beads was added to the entire 15 uL digestion reaction performed previously and the tag and anti-tag hybridization reaction was allowed to proceed at 37° C. for 30 minutes. Following hybridization, 75 µL of 1-in-500 diluted streptavidin-Phycoerytherin was added and the reaction was incubated at room temperature for 15 minutes. The bead bound amplification products were then analyzed on the Luminex instrument. The MFI values for undigested amplification product shown in Table 1 are essentially without significance because the segregation to each respective bead can be erratic or bridging across two bead species (doublets) can occur. Following Taq1 digestion, the ratios became more evident for the male genomic samples shown.

The relative length of the expansion region is reflected in the expansion region fragment while the other fragment represents an internal control. As is reflected in the results, typically as the trinucleotide expansion increases, the amplification product size increases, resulting in overall lower MFIs. The wildtype sample containing a repeat size of 20 produced a signal intensity of 411 for the expansion control fragment and a signal intensity of 213 for the internal control fragment, and therefore exhibited a ratio of 1.93. The expanded sample containing a repeat size of 117 showed a signal intensity of 114 for the expansion control fragment and a signal intensity of 54 for the internal control fragment, and therefore exhibited a ratio of 2.11. Finally, the expanded sample containing a repeat size of 80-85 showed a signal intensity of 291 for the expansion control fragment and a signal intensity of 137 for the internal control fragment, and therefore exhibited a ratio of 2.12. These results are summarized in Table 1.

TABLE 1

| Sample | 076-FMR1 forward | 077-FMR1-Reverse | ratio F/R | (CGG)n repeat size | gender | Coriell # |
|---|---|---|---|---|---|---|
| T1-TAQ | 411 | 213 | 1.93 | 20 | male | / |
| T1-UNCUT | 379 | 467.5 | / | 20 | male | / |
| C3-TAQ1 | 114 | 54 | 2.11 | 117 | male | NA06891 |
| C3-UNCUT | 137 | 141 | / | 117 | male | NA06891 |
| C4-TAQ1 | 291 | 137 | 2.12 | 80-85 | male | NA06892 |
| C4-UNCUT | 294.5 | 310 | / | 80-85 | male | NA06892 |
| BLK-TAQ1 | 45 | 38 | / | / | / | / |
| BLK-UNCUT | 45 | 37 | / | / | / | / |

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the methods described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 4,284,412
U.S. Pat. No. 4,498,766
U.S. Pat. No. 4,659,774
U.S. Pat. No. 4,661,913
U.S. Pat. No. 4,682,195
U.S. Pat. No. 4,683,202
U.S. Pat. No. 4,714,682
U.S. Pat. No. 4,767,206
U.S. Pat. No. 4,774,189
U.S. Pat. No. 4,816,571
U.S. Pat. No. 4,857,451
U.S. Pat. No. 4,883,750
U.S. Pat. No. 4,942,124
U.S. Pat. No. 4,959,463
U.S. Pat. No. 4,989,977
U.S. Pat. No. 5,141,813
U.S. Pat. No. 5,160,974
U.S. Pat. No. 5,264,566
U.S. Pat. No. 5,428,148
U.S. Pat. No. 5,478,722
U.S. Pat. No. 5,525,494
U.S. Pat. No. 5,539,082
U.S. Pat. No. 5,554,744
U.S. Pat. No. 5,574,146
U.S. Pat. No. 5,602,244
U.S. Pat. No. 5,645,897
U.S. Pat. No. 5,654,413
U.S. Pat. No. 5,705,629
U.S. Pat. No. 5,714,331
U.S. Pat. No. 5,719,262
U.S. Pat. No. 5,736,330
U.S. Pat. No. 5,736,336
U.S. Pat. No. 5,766,855
U.S. Pat. No. 5,773,571
U.S. Pat. No. 5,786,461
U.S. Pat. No. 5,837,832
U.S. Pat. No. 5,837,860
U.S. Pat. No. 5,840,873
U.S. Pat. No. 5,843,640
U.S. Pat. No. 5,843,650
U.S. Pat. No. 5,843,651
U.S. Pat. No. 5,846,708
U.S. Pat. No. 5,846,709
U.S. Pat. No. 5,846,717
U.S. Pat. No. 5,846,726
U.S. Pat. No. 5,846,729
U.S. Pat. No. 5,846,783
U.S. Pat. No. 5,849,487
U.S. Pat. No. 5,849,497
U.S. Pat. No. 5,849,546
U.S. Pat. No. 5,849,547
U.S. Pat. No. 5,853,990
U.S. Pat. No. 5,853,992
U.S. Pat. No. 5,853,993
U.S. Pat. No. 5,856,092
U.S. Pat. No. 5,858,652
U.S. Pat. No. 5,861,244
U.S. Pat. No. 5,863,732
U.S. Pat. No. 5,863,753
U.S. Pat. No. 5,866,331
U.S. Pat. No. 5,866,366
U.S. Pat. No. 5,882,864
U.S. Pat. No. 5,891,625
U.S. Pat. No. 5,905,024
U.S. Pat. No. 5,908,845
U.S. Pat. No. 5,910,407
U.S. Pat. No. 5,912,124
U.S. Pat. No. 5,912,145
U.S. Pat. No. 5,912,148
U.S. Pat. No. 5,916,776
U.S. Pat. No. 5,916,779
U.S. Pat. No. 5,919,630

U.S. Pat. No. 5,922,574
U.S. Pat. No. 5,925,517
U.S. Pat. No. 5,928,862
U.S. Pat. No. 5,928,869
U.S. Pat. No. 5,928,905
U.S. Pat. No. 5,928,906
U.S. Pat. No. 5,929,227
U.S. Pat. No. 5,932,413
U.S. Pat. No. 5,932,451
U.S. Pat. No. 5,935,791
U.S. Pat. No. 5,935,825
U.S. Pat. No. 5,939,291
U.S. Pat. No. 5,942,391
U.S. Pat. No. 5,981,180
U.S. Pat. No. 6,057,107
U.S. Pat. No. 6,103,463
U.S. Pat. No. 6,322,971
U.S. Pat. No. 7,226,737
U.S. Pub. Appln. 2005/0191625
Egholm et al., *Nature*, 365(6446):566-568, 1993.
European Appln. 266032
European Appln. 320 308
European Appln. 329 822
Fodor et al., *Biochemistry*, 30(33):8102-8108, 1991.
Froehler et al., *Nucleic Acids Res.*, 14:5399-5407, 1986.
Frohman, In: *PCR Protocols: A Guide To Methods And Applications*, Academic Press, N.Y., 1990.
Gatta et al., *Hum. Genet.*, 117(1):92-98, 2005.
GB Appln. 2 202 328
Holmstrom et al., *Anal. Biochem.* 209:278-283, 1993.
Koshkin and Dunford, *J. Biol. Chem.*, 273(11):6046-6049, 1998a.
Koshkin and Wengel, *J. Org. Chem.*, 63(8):2778-2781, 1998b.
Kwoh et al., *Proc. Natl. Acad. Sci. USA*, 86:1173, 1989.
Moseley et al., *Hum. Mol. Gen.*, 9: 2125-2130, 2000.
Mueller et al, *Current Protocols in Mol. Biol.*; 15:5, 1993.
Newton et al., *Nucl. Acids Res.* 21:1155-1162, 1993.
Ohara et al., *Proc. Natl. Acad. Sci. USA*, 86:5673-5677, 1989.
PCT Appln. PCT/EP/01219
PCT Appln. PCT/US87/00880
PCT Appln. PCT/US89/01025
PCT Appln. WO 88/10315
PCT Appln. WO 89/06700
PCT Appln. WO 90/07641
PCT Appln. WO 92/20702
PCT Appln. WO 93/17126
PCT Appln. WO 97/31256
Pease et al., *Proc. Natl. Acad. Sci. USA*, 91:5022-5026, 1994.
Rasmussen et al., *Anal. Biochem*, 198:138-142, 1991.
Running et al., *BioTechniques* 8:276-277, 1990.
Sambrook et al., In: *Molecular cloning*, Cold Spring Harbor Laboratory Press, Cold Spring Harbor, N.Y., 2001.
Santalucia et al., *Biochemistry;* 38:3468-77, 1999.
Wahlestedt et al., *Proc. Natl. Acad. Sci. USA*, 97(10):5633-5638, 2000.
Walker et al., *Proc. Natl. Acad. Sci. USA*, 89:392-396, 1992.

What is claimed is:

1. A method for evaluating the length of a trinucleotide repeat region on an X chromosome, said method comprising:
    (a) amplifying a trinucleotide repeat region on the X chromosome with a primer pair, each primer of the primer pair comprising a target specific sequence, a differentiating tag sequence 5' of the target specific sequence and a blocker between the target specific sequence and the differentiating tag sequence to produce a dual-tagged amplification product;
    (b) labeling the dual-tagged amplification product;
    (c) digesting the dual-tagged amplification product with a restriction enzyme to produce a trinucleotide repeat region fragment and an internal control fragment;
    (d) hybridizing the trinucleotide repeat region fragment to a first capture complex comprising an anti-tag sequence and a solid support, and hybridizing the internal control fragment to a second capture complex comprising an anti-tag sequence and a solid support;
    (e) detecting a signal produced by the label on the immobilized trinucleotide repeat region fragment and a signal produced by the label on the internal control fragment; and
    (f) comparing the intensity of the signal of the trinucleotide repeat region fragment and the signal of the internal control fragment to evaluate the length of the trinucleotide repeat region on the X chromosome.

2. The method of claim 1, wherein the trinucleotide repeat region is a trinucleotide repeat region of an FMR1 gene, an FMR2 gene or an Androgen Receptor gene.

3. The method of claim 1, wherein labeling the dual-tagged amplification product occurs during amplification.

4. The method of claim 1, wherein labeling the dual-tagged amplification product occurs after amplification.

5. The method of claim 1, wherein the length of the trinucleotide repeat region is evaluated semi-quantitatively as being normal, pre-expansion, or expanded.

6. The method of claim 1, wherein the solid support is a bead.

7. The method of claim 6, wherein the bead is a fluorescently labeled bead.

8. The method of claim 1, wherein detecting the signal produced by the label of the immobilized trinucleotide region fragment and the label of the internal control fragment comprises flowing the fragments through a flow cytometer.

9. A method for evaluating the length of a (CGG)$_n$ trinucleotide repeat region within an FMR1 gene, said method comprising:
    (a) amplifying a (CGG)$_n$ trinucleotide repeat region within an FMR1 gene with a primer pair, each primer of the primer pair comprising a target specific sequence, a differentiating tag sequence 5' of the target specific sequence and a blocker between the target specific sequence and the differentiating tag sequence to produce a dual-tagged amplification product;
    (b) labeling the dual-tagged amplification product;
    (c) digesting the dual-tagged amplification product with a restriction enzyme to produce a (CGG)$_n$ trinucleotide repeat region fragment and an internal control fragment;
    (d) hybridizing the trinucleotide repeat region fragment to a first capture complex comprising an anti-tag sequence and a solid support, and hybridizing the internal control fragment to a second capture complex comprising an anti-tag sequence and a solid support;

(e) detecting a signal produced by the label on the immobilized trinucleotide repeat region fragment and a signal produced by the label on the internal control fragment; and (f) comparing the intensity of the signal of the $(CGG)_n$ trinucleotide repeat region fragment and the signal of the internal control fragment to evaluate the length of the $(CGG)_n$ trinucleotide repeat region within the FMR1 gene.

10. The method of claim 9, wherein labeling the dual-tagged amplification product occurs during amplification.

11. The method of claim 10, wherein the label is Biotin-dCTP.

12. The method of claim 9, wherein the solid support is a bead.

13. The method of claim 12, wherein the bead is a fluorescently labeled bead.

14. A method for diagnosing a trinucleotide expansion disease on the X chromosome comprising:
   (a) obtaining a nucleic acid sample from a subject to be tested;
   (b) amplifying a target nucleic acid sequence in the sample with a primer pair, each primer of the primer pair comprising a target specific sequence, a differentiating tag sequence 5' of the target specific sequence and a blocker between the target specific sequence and the differentiating tag sequence to produce a dual-tagged amplification product;
   (c) labeling the dual-tagged amplification product;
   (d) digesting the dual-tagged amplification product with a restriction enzyme to produce an expansion region fragment and an internal control fragment;
   (e) hybridizing the expansion region fragment to a first capture complex comprising an anti-tag sequence and a solid support, and hybridizing the internal control fragment to a second capture complex comprising an anti-tag sequence and a solid support;
   (f) detecting a signal produced by the label on the immobilized expansion region fragment and a signal produced by the label on the internal control fragment; and
   (g) comparing the intensity of the signal of the expansion region fragment and the signal of the internal control fragment to diagnose a trinucleotide expansion disease if the intensity of the signal of the expansion region fragment is above a pre-determined threshold value.

15. The method of claim 14, wherein the disease is Fragile-X syndrome, Fragile XE mental retardation, or spinobulbar muscular atrophy.

16. A method for diagnosing Fragile-X syndrome comprising:
   (a) obtaining a nucleic acid sample from a subject to be tested;
   (b) amplifying a $(CGG)_n$ expansion region within an FMR1 gene in the nucleic acid sample with a primer pair, each primer of the primer pair comprising a target specific sequence, a differentiating tag sequence 5' of the target specific sequence and a blocker between the target specific sequence and the differentiating tag sequence to produce a dual-tagged amplification product;
   (c) labeling the dual-tagged amplification product;
   (d) digesting the dual-tagged amplification product with a restriction enzyme to produce an expansion region fragment and an internal control fragment;
   (e) hybridizing the expansion region fragment to a first capture complex comprising an anti-tag sequence and a solid support, and hybridizing the internal control fragment to a second capture complex comprising an anti-tag sequence and a solid support;
   (f) detecting a signal produced by the label on the immobilized expansion region fragment and a signal produced by the label on the internal control fragment; and
   (g) comparing the intensity of the signal of the expansion region fragment and the signal of the internal control fragment to diagnose Fragile-X syndrome if the intensity of the signal of the expansion region fragment is above a pre-determined threshold value.

17. The method of claim 16, wherein the subject is male.

18. The method of claim 16, wherein the primer pair comprises SEQ ID NO:1 and SEQ ID NO:2.

19. The method of claim 16, wherein labeling the dual-tagged amplification product occurs during amplification.

20. The method of claim 19, wherein the label is Biotin-dCTP.

21. The method of claim 16, wherein the restriction enzyme is TaqI.

22. A kit for evaluating a trinucleotide repeat region on the X chromosome comprising:
   (a) a primer pair capable of amplifying a trinucleotide repeat region on the X chromosome, each primer of the primer pair comprising a target specific sequence, a differentiating tag sequence 5' of the target specific sequence and a blocker between the target specific sequence and the differentiating tag sequence;
   (b) a label;
   (c) a pair of capture complexes, each comprising an anti-tag sequence and a solid support; and
   (d) a restriction enzyme capable of cleaving an amplification product produced by said primer pair into a trinucleotide repeat region fragment and an internal control fragment.

23. The kit of claim 22, wherein the trinucleotide repeat is the $(CGG)_n$ expansion region within the FMR1 gene.

24. The kit of claim 22, wherein one primer of the primer pair comprises the nucleic acid sequence of SEQ ID NO:1 and the other primer of the primer pair comprises the nucleic acid sequence of SEQ ID NO:2.

* * * * *

UNITED STATES PATENT AND TRADEMARK OFFICE
CERTIFICATE OF CORRECTION

PATENT NO. : 8,008,019 B2
APPLICATION NO. : 12/277768
DATED : August 30, 2011
INVENTOR(S) : Frank Merante et al.

It is certified that error appears in the above-identified patent and that said Letters Patent is hereby corrected as shown below:

In claim 9, column 28, line 49, delete "(CGG)," and insert --$(CGG)_n$-- therefor.

In claim 9, column 29, line 8, delete "(CGG)," and insert --$(CGG)_n$-- therefor.

In claim 16, column 29, line 53, delete "(CGG)," and insert --$(CGG)_n$-- therefor.

Signed and Sealed this
Third Day of January, 2012

David J. Kappos
*Director of the United States Patent and Trademark Office*